US 11,266,820 B1

(12) United States Patent
Bridge

(10) Patent No.: US 11,266,820 B1
(45) Date of Patent: Mar. 8, 2022

(54) NASAL AND PHARYNGEAL PALATAL SUPPORT

(71) Applicant: Robert S. Bridge, Scottsdale, AZ (US)

(72) Inventor: Robert S. Bridge, Scottsdale, AZ (US)

( * ) Notice: Subject to any disclaimer, the term of this patent is extended or adjusted under 35 U.S.C. 154(b) by 159 days.

(21) Appl. No.: 15/872,268

(22) Filed: Jan. 16, 2018

Related U.S. Application Data

(62) Division of application No. 14/102,982, filed on Dec. 11, 2013, now Pat. No. 9,901,723.

(60) Provisional application No. 61/736,088, filed on Dec. 12, 2012.

(51) Int. Cl.
| | |
|---|---|
| *A61M 29/00* | (2006.01) |
| *A61F 5/08* | (2006.01) |
| *A61M 25/02* | (2006.01) |
| *A61F 5/56* | (2006.01) |
| *A61M 16/06* | (2006.01) |
| *A61B 17/24* | (2006.01) |
| *A61F 13/20* | (2006.01) |

(52) U.S. Cl.
CPC ............. *A61M 29/00* (2013.01); *A61F 5/08* (2013.01); *A61B 17/24* (2013.01); *A61B 2017/246* (2013.01); *A61B 2017/248* (2013.01); *A61F 5/56* (2013.01); *A61F 13/2005* (2013.01); *A61M 16/0666* (2013.01); *A61M 2025/0226* (2013.01)

(58) Field of Classification Search
None
See application file for complete search history.

(56) References Cited

U.S. PATENT DOCUMENTS 4,883,465 A * 11/1989 Brennan ............... A61M 27/00
604/96.01

* cited by examiner

*Primary Examiner* — Shaun L David
(74) *Attorney, Agent, or Firm* — Skinner and Associates; Joel D. Skinner, Jr.

(57) ABSTRACT

A system includes a platform configured for insertion into a user's nostril and a catheter. The platform includes a board having first and second major surfaces and a support extending from the board. The support includes an aperture therethrough. The catheter includes an inflatable tube and a lumen having first and second ends, the first end connected to the tube and the second end connected to a pressurized fluid source for inflating the tube. The tube is configured for insertion through the aperture. A method includes inserting a platform into a user's nostril, inserting a catheter through an aperture of the platform, and inflating a tube of the catheter. Inflating the tube is accomplished by introducing a pressurized fluid through a lumen of the catheter, to thereby cause the tube to conform to a passage of the user's nasal or pharyngeal region.

8 Claims, 7 Drawing Sheets

NASAL AND PHARYNGEAL PALATAL SUPPORT

CROSS REFERENCE TO RELATED APPLICATIONS

This application is a divisional application of U.S. patent application Ser. No. 14/102,982, filed on Dec. 11, 2013, which claims the benefit of priority from U.S. Provisional Patent Application No. 61/736,088, filed Dec. 12, 2012, which are fully incorporated by reference herein.

SUMMARY

In one aspect, a system comprises a platform configured for insertion into a user's nostril and a catheter. The platform comprises a board having first and second major surfaces and a support extending from the board. The support comprises an aperture therethrough. The catheter comprises an inflatable tube and a lumen having first and second ends, the first end connected to the tube and the second end connected to a pressurized fluid source for inflating the tube. The tube is configured for insertion through the aperture.

In another aspect, an apparatus is configured for insertion into a user's nostril. The apparatus comprises a board having first and second major surfaces and first and second ends and a first support extending from the board proximate the first end. The first support comprises a first aperture therethrough.

In yet another aspect, a method comprises inserting a platform into a user's nostril, inserting a catheter through an aperture of the platform, and inflating a tube of the catheter. The platform comprises a board having first and second major surfaces and a support extending from the board, the support comprising an aperture therethrough. The catheter comprises an inflatable tube and a lumen having first and second ends, the first end connected to the tube and the second end connected to a pressurized fluid source for inflating the tube. Inflating the tube is accomplished by introducing a pressurized fluid through the lumen, to thereby cause the tube to conform to a passage of the user's nasal or pharyngeal region.

This disclosure, in its various combinations, either in apparatus or method form, may also be characterized by the following listing of items:
1. A system comprising:
a platform configured for insertion into a user's nostril, the platform comprising:
 a board having first and second major surfaces; and
 a support extending from the board, the support comprising an aperture therethrough; and
 a catheter comprising:
 an inflatable tube; and
 a lumen having first and second ends, the first end connected to the tube and the second end connected to
 a pressurized fluid source for inflating the tube;
wherein the tube is configured for insertion through the aperture.
2. The system of item 1 wherein at least one of the first and second major surfaces of the board is curved.
3. The system of any of items 1-2 wherein the platform comprises a guide disposed on the board.
4. The system of item 3 wherein the guide comprises a channel therethrough.
5. The system of any of items 1-4 wherein the support is substantially triangular.
6. The system of any of items 1-5 wherein the support is inflatable.
7. The system of any of items 1-6 wherein at least a portion of the board is inflatable.
8. An apparatus configured for insertion into a user's nostril, the apparatus comprising:
 a board having first and second major surfaces and first and second ends; and
 a first support extending from the board proximate the first end, the first support comprising a first aperture therethrough.
9. The apparatus of item 8 wherein at least one of the first and second major surfaces of the board is curved.
10. The apparatus of any of items 8-9 further comprising a guide disposed on the board.
11. The apparatus of item 10 wherein the guide comprises a channel therethrough.
12. The apparatus of any of items 10-11 wherein the guide comprises a plurality of elements extending from the board.
13. The apparatus of any of items 8-12 further comprising a second support extending from the board proximate the second end, the second support comprising a second aperture therethrough.
14. The apparatus of item 13 wherein at least one of the first and second supports is substantially triangular.
15. The apparatus of any of items 8-14 wherein at least one of the first and second supports is inflatable.
16. The apparatus of any of items 8-15 wherein at least a portion of the board is inflatable.
17. A method comprising:
inserting a platform into a user's nostril, the platform comprising:
 a board having first and second major surfaces; and
 a support extending from the board, the support comprising an aperture therethrough;
inserting a catheter through the aperture, the catheter comprising:
 an inflatable tube; and
 a lumen having first and second ends, the first end connected to the tube and the second end connected to
 a pressurized fluid source for inflating the tube; and
inflating the tube by introducing a pressurized fluid through the lumen, to thereby cause the tube to conform to a passage of the user's nasal or pharyngeal region.
18. The method of item 17 further comprising fitting a curved portion of the board to the user's palate.
19. The method of any of items 17-18 further comprising guiding the catheter through a guide disposed on the board.
20. The method of any of items 17-19 further comprising inflating at least a portion of the board.

This summary is provided to introduce concepts in simplified form that are further described below in the Detailed Description. This summary is not intended to identify key features or essential features of the disclosed or claimed subject matter and is not intended to describe each disclosed embodiment or every implementation of the disclosed or claimed subject matter. Specifically, features disclosed herein with respect to one embodiment may be equally applicable to another. Further, this summary is not intended to be used as an aid in determining the scope of the claimed subject matter. Many other novel advantages, features, and relationships will become apparent as this description proceeds. The figures and the description that follow more particularly exemplify illustrative embodiments.

BRIEF DESCRIPTION OF THE DRAWINGS

The disclosed subject matter will be further explained with reference to the attached figures, wherein like structure

While the above-identified figures set forth one or more embodiments of the disclosed subject matter, other embodiments are also contemplated, as noted in the disclosure. In all cases, this disclosure presents the disclosed subject matter by way of representation and not limitation. It should be understood that numerous other modifications and embodiments can be devised by those skilled in the art which fall within the scope and spirit of the principles of this disclosure.

The figures may not be drawn to scale. In particular, some features may be enlarged relative to other features for clarity. Moreover, where terms such as above, below, over, under, top, bottom, side, right, left, etc., are used, it is to be understood that they are used only for ease of understanding the description. It is contemplated that structures may be oriented otherwise.

DETAILED DESCRIPTION

This disclosure is directed to a secure nasal and pharyngeal palatal support platform on which different sized catheter driven inflatable devices (such as balloons and/or elliptical or triangular donuts or tubes, for example) can be used in multiple applications including, for example, snoring reduction, airway control for obtunded anesthesia patients, directed epistaxis control, and as a guide for insertion of an irrigation device for rinsing thick post nasal drainage.

Figure 1:
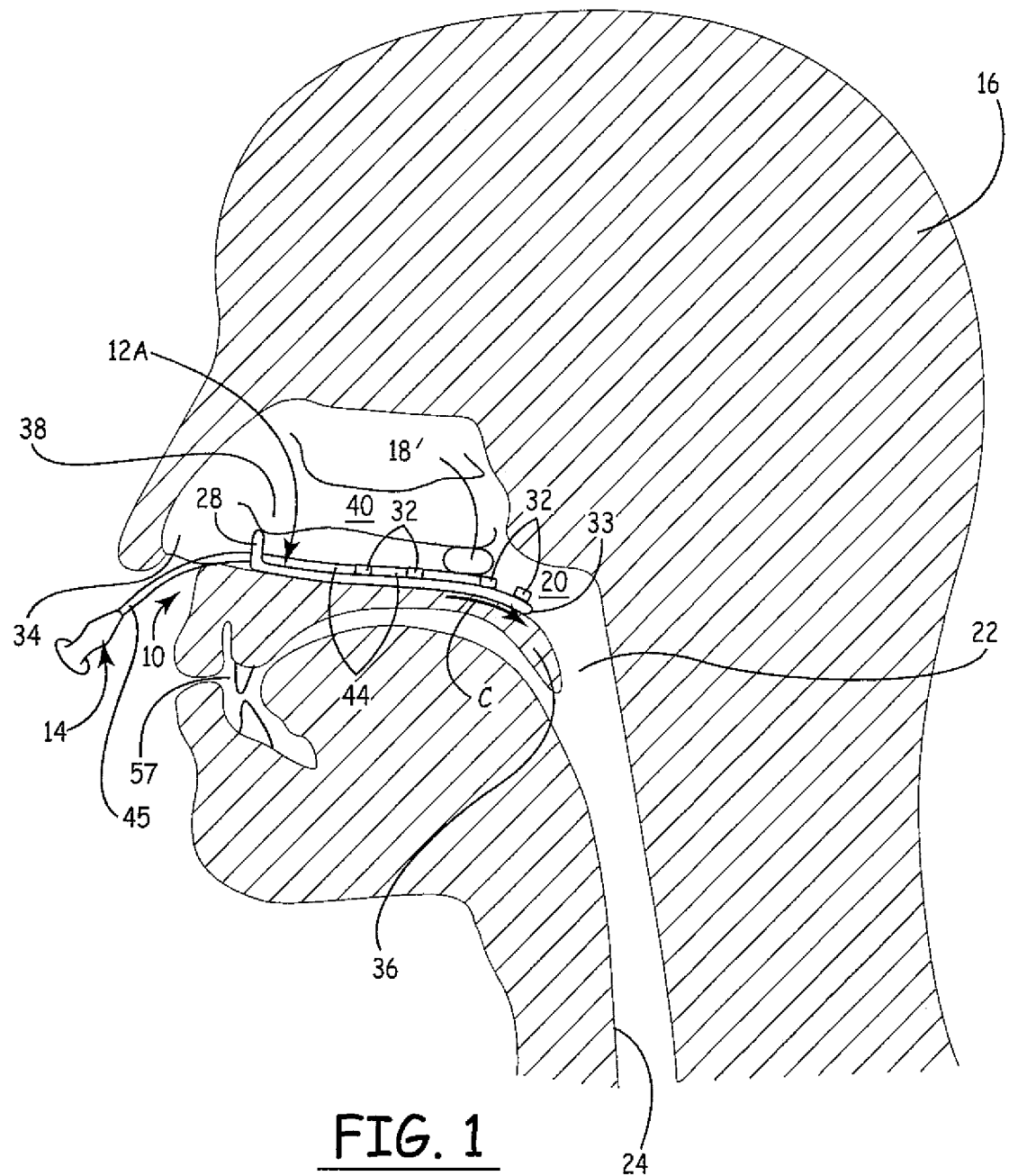
FIG. 1 is a sectional side view of a user having placed within his nasal cavity a first embodiment of a platform and balloon catheter system of the present disclosure.

This disclosure is directed to a nasal and pharyngeal palatal support system 10 including a platform 12 configured for insertion into nostril 34 of user 16 and a balloon catheter 14, as shown in FIG. 1. The system 10 is used to place the inflatable tube 18 of the balloon catheter in a desired location in the user's nasal cavity 20 or pharynx 22, and/or at the base of the tongue 24. In the disclosure, the term "anterior" generally refers to a direction proximate or toward the user's nostril 34; the term "posterior" generally refers to a direction proximate or toward the user's throat.

Figure 2:
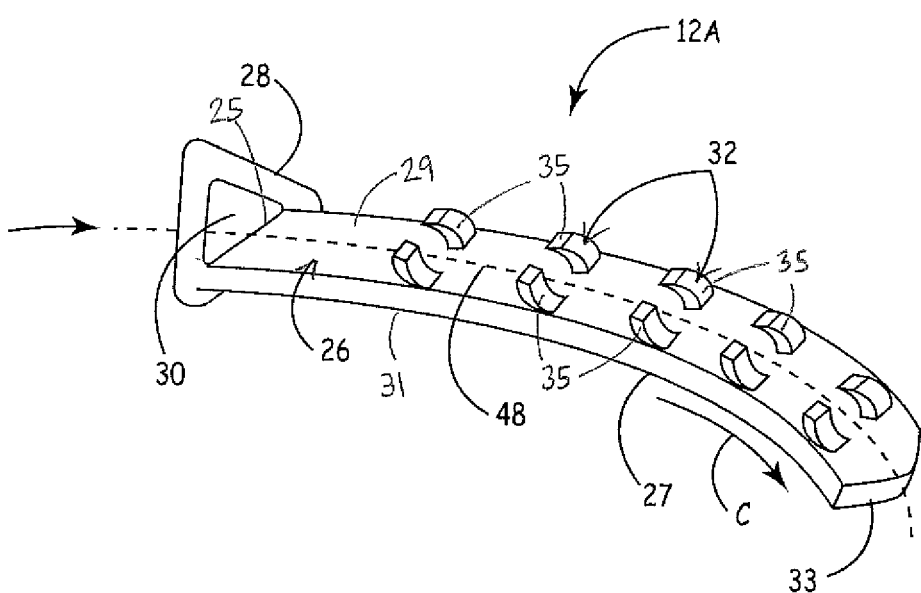
FIG. 2 is a top perspective view of a first embodiment of an exemplary platform.

FIG. 2 is a perspective view of a first exemplary platform 12A, which has anterior end 25 and posterior end 33. In an exemplary embodiment, platform 12A includes a board 26 having first major surface 29 and second major surface 31. Anterior support 28 extends substantially perpendicularly from board 26 proximate anterior end 25. In an exemplary method of use, a doctor performs nasal endoscopy on a patient to measure and fit the platform 12A to the patient. Board 26 is typically formed of plastic and is typically about 4 mm wide, about 2 mm thick, and about 4 cm to about 5 cm long.

In an exemplary embodiment, board 26 has a downward curve 27 in one or both of first major surface 29 and second major surface 31. Curve 27 is disposed adjacent posterior end 33 of platform 12 so that platform 12 better conforms to and fits snugly over the natural contours of a patient's nasopharyngeal region (e.g., the drop-off of the posterior floor of the nasal cavity into the nasopharyngeal region). Board 26 is sufficiently flexible to be comfortably inserted and removed, and ends and side edges are rounded or curved to facilitate such insertion and removal. For enhanced comfort, board 26 may be partially or entirely inflatable or otherwise expandable so that it is more compact during insertion and removal but assumes its full intended configuration (such as illustrated in FIG. 2) once in position. Anterior support 28 is made of a flexible yet supportive and stable material such as soft rubber and in some cases is inflatable. In an exemplary embodiment, anterior support is an annulus with a substantially triangular shape to mimic and comfortably fit into the user's nostril 34 and nasal passages. Anterior support 28 has an aperture 30 for airflow therethrough. In those embodiments where board 26 (or a portion thereof) and/or anterior support 28 are inflatable, suitable inflation fluid connections and lumens are provided adjacent the anterior end of board 26.

Figure 3:
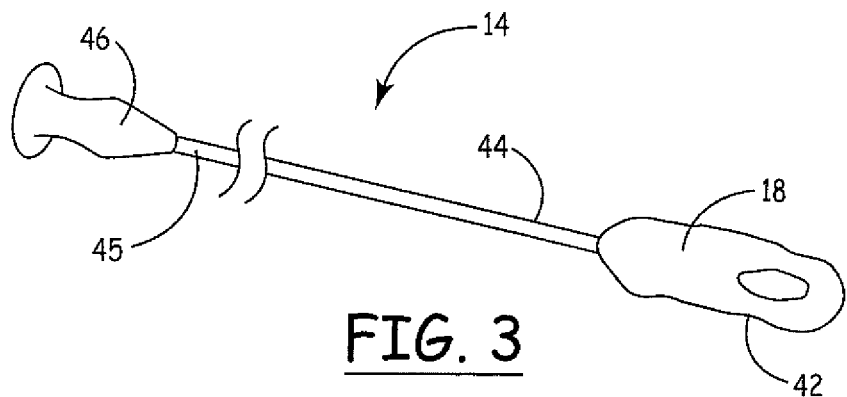
FIG. 3 is a perspective view of an exemplary balloon catheter of the present disclosure, with the tube deflated.
Figure 9A:
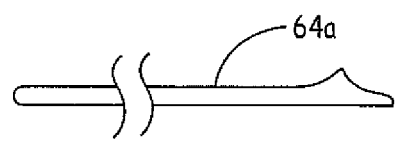
FIGS. 9a and 9b are side views of two exemplary pusher configurations.
Figure 9B:
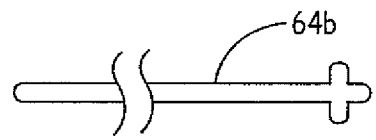

Platform 12A has a plurality of guides 32 for guiding a balloon catheter 14, as shown in FIG. 3, into position. In an exemplary embodiment, each guide 32 comprises a pair of elements 35 extending from board 26. Referring to FIGS. 1-3, a user 16 uses the system 10 by first inserting posterior end 33 of platform 12 into his/her nostril 34 and pushing platform 12 along the floor of his/her palate 36 until anterior support 28 is firmly lodged against the anterior aspect 38 of his/her inferior turbinate 40, such as at the ridge of the limen nasi. Inflatable tube 18 is connected to first end 42 of lumen 44. The user 16 guides first end 42 of a lumen 44 of balloon catheter 14 along path 48 through aperture 30 of anterior support 28 and through guides 32 of board 26 until inflatable tube 18 is in the desired position. The plurality of guides 32 are spaced closely enough to define a path 48 therethrough for guidance of the lumen 44, such as at 1.0 cm intervals. Lumen 44 in an exemplary embodiment is stiff enough for insertion through guides 32. In other embodiments, a pusher 64 (exemplary embodiments of which are shown in FIGS. 9a and 9b) is used to advance the balloon catheter 14 by engaging a hole or channel 50 in the balloon catheter 14 and pushing the balloon catheter 14 along path 48, moving slowly posterior until the desired position is reached. Pusher 64 is then removed from the nasal cavity.

FIG. 3 shows a dilator such as inflatable tube 18 in a deflated state, as it will be in during insertion and removal of balloon catheter 14. In this configuration, the uninflated balloon has a low profile to facilitate insertion and movement relative to board 26 and its associated guides 32. Lumen 44 may be centered under deflated tube 18 or may be offset to the left or right for optimal placement after guidance through either the left or right nostril. In another method of use, balloon catheter may be pre-loaded onto platform 12 before platform 12 is inserted into the user's nostril 34.

Figure 4:
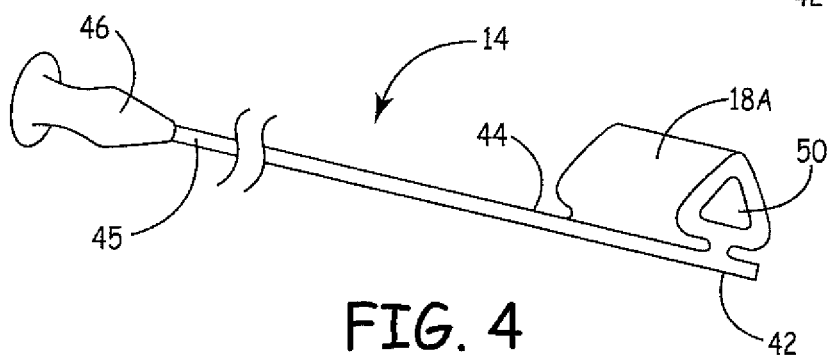
FIG. 4 is a perspective view of a first embodiment of a balloon catheter of the present disclosure, with the tube inflated.

In an exemplary embodiment, lumen 44 is connected at its second end (i.e., its anterior end) to luer lock tubing 45, which is in turn connected to luer lock fitting 46 for attachment to a fluid source such as a pump or syringe for inflation of tube 18. In an exemplary embodiment, a length of lumen 44 and luer lock tubing 45 is from about 5.0 cm to about 7.0 cm. In one embodiment, each guide 32 is open at its top to allow tube 18 to inflate on top of the guide 32. Luer lock fitting 46 is connected to a pressurized fluid source for inflating tube 18. The user then inflates tube 18 via the introduction of the pressurized fluid through lumen 44. FIG. 4 is a perspective view of a first exemplary tube 18A in an inflated state.

Figure 5:
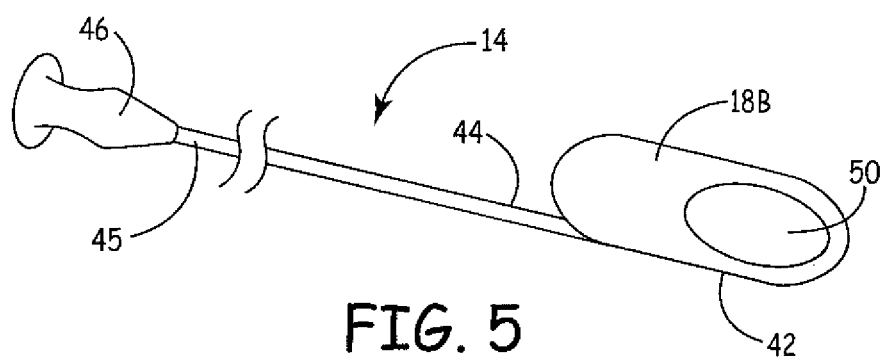
FIG. 5 is a perspective view of a second embodiment of a balloon catheter of the present disclosure, with the tube inflated.
Figure 6:
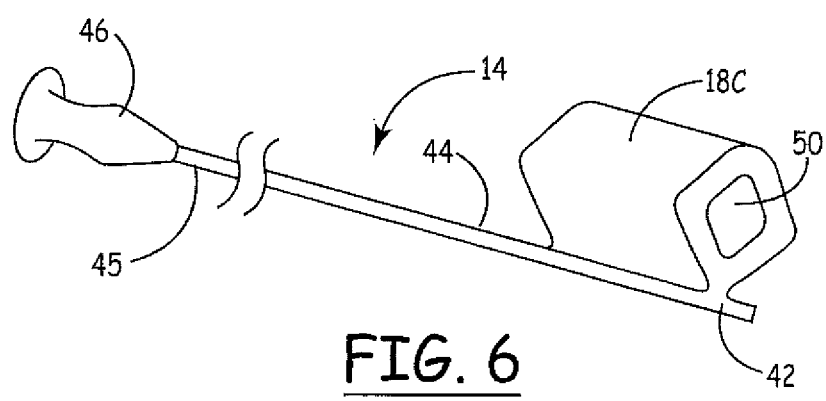
FIG. 6 is a perspective view of a third embodiment of a balloon catheter of the present disclosure, with the tube inflated.

While the term "tube" is used, the configuration is not limited to a cylindrical shape. For example, the illustrated tube 18A has a substantially triangular cross-sectional shape to closely conform to the contours of the nasal passages. While a generally isosceles triangle is illustrated, a right triangle or other shapes may be used to more specifically conform to particular portions of the user's anatomy. FIG. 5 shows another exemplary inflated tube 18B having a substantially elliptical cross-section. FIG. 6 shows another exemplary inflated tube 18C having a substantially rhombus cross-section. Each tube 18 has a channel 50 therethrough for permitting airflow through the inflated tube 18. Typically, such a tube 18 has a length of about 1.0 cm to about 2.0 cm or a length of about 2.0 cm to about 2.5 cm, depending on the user's anatomy and the placement position either in the nasal passageway or in the nasopharynx. When the inflatable tube 18 is inflated, it typically has a wall thickness of about 2 mm to about 5 mm and an average diameter of channel 50 of about 1.0 cm to about 1.7 cm.

The placement of tube 18' as shown in FIG. 1 is especially suitable for tamponade of epistaxis (i.e., stopping nosebleed). The tube 18' can be placed precisely at the bleeding site without unduly obstructing air flow to and through the nose. Because tube 18' is typically deflated during insertion into nostril 34, insertion of balloon catheter 14 using platform 12A is more easily accomplished and positioning can be more precise than with currently available nose packs (which are also air flow obstructive). Moreover, inflation of tube 18' after positioning allows the tube 18A to conform specifically to the contours of that portion of the nasal passage (typically between the septum, middle and inferior turbinates), leading to more efficient tamponade and greater user comfort.

In one embodiment, tube 18' has a substantially triangular cross section when inflated to conform to the contours of some areas of the nasal passageway to thereby efficiently apply pressure to the nasal walls. Other areas of the nasal passageway have a different shape and may be better served by the substantially rhombus cross-sectional shape of tube 18C (FIG. 6) to conform specifically to the contours of that portion of the nasal passage, leading to more efficient tamponade and greater user comfort. Inflatable tubes 18 of other shapes may also be used to conform to the particular anatomy of a body passageway. In an exemplary embodiment, for use in stopping nosebleeds, each of tubes 18 is tall enough (in the range of about 0.5 cm to about 2.0 cm) to apply pressure in the upper septal region adjacent to the middle turbinate.

Because it is often difficult to initially pinpoint an exact location of bleeding, an advantage of system 10 is that tube 18' is easily deflated, repositioned, and re-inflated if an initial placement is ineffective. Moreover, while a single tube 18' is shown in a relatively posterior position in the nasal cavity, it is to be understood that the position of tube 18' may be anterior to that shown and that two or more tubes 18' may be used simultaneously (on a single inflation lumen, or on multiple separate inflation lumens) to increase the ease with which the bleeding will be stopped. In contrast to current methods, the disclosed system and method for tamponade of epistaxis effectively stops bleeding without placing so much pressure on the septum that it collapses into the other nostril.

Figure 7:
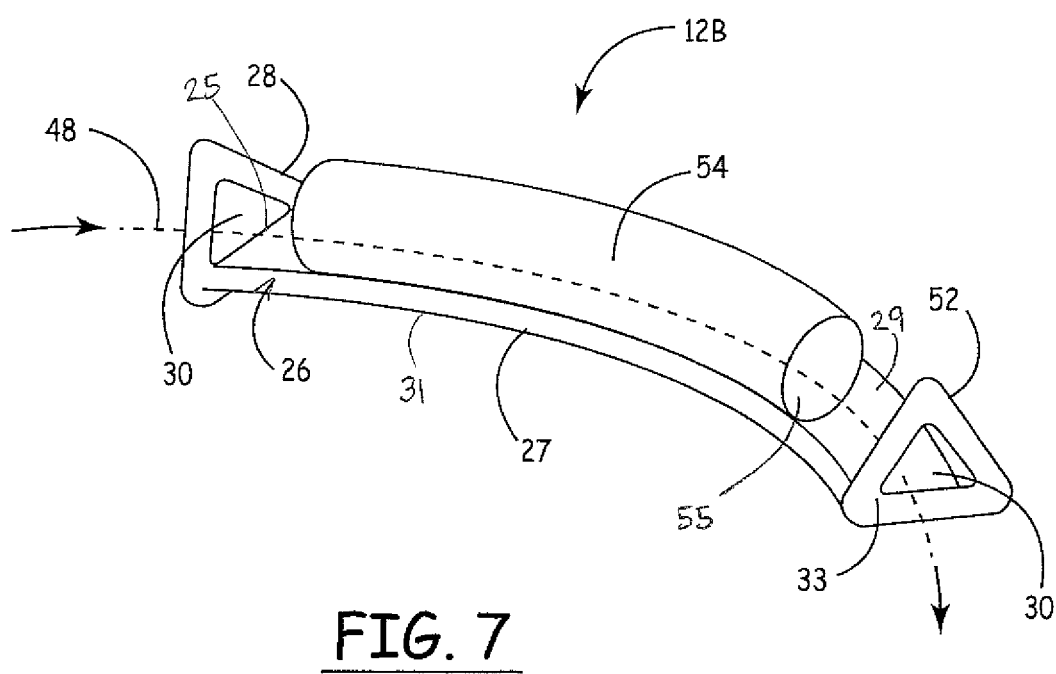
FIG. 7 is a top perspective view of a second embodiment of an exemplary platform.

FIG. 7 is a perspective view of a second exemplary embodiment of platform 12B, which has anterior support 28, posterior support 52, and tunnel 54 for the guidance of balloon catheter 14 along path 48. Posterior support 52 extends substantially perpendicularly from board 28 for additional support of the nasal or pharyngeal region proximate posterior end 33 of platform 12B. This is especially suitable for applications where tube(s) 18 are positioned farther posterior into the pharynx, rather than in the nasal cavity. However, a platform 12 can have both anterior support 28 and posterior support 52 even if tube(s) 18 are positioned more anteriorly (as in FIG. 1 or anterior to the position of tube 18' in FIG. 1).

Posterior support 52 is illustrated as having a triangular shape like anterior support 28. However, it may also have other shapes to conform to the particular area of the nasal cavity or pharynx in which it will be used. Other suitable shapes include a substantially elliptical, circular, square, rhombus or rectangular shapes with an aperture 30 therethrough. Posterior support 52 is made of a flexible yet supportive and stable material such as soft rubber and in some cases is inflatable. In exemplary embodiments, edges of the platform 12 are rounded or curved for user comfort, tolerance, and ease of use. The provision of tunnel 54 having channel 55 therethrough as a guide for balloon catheter 14 is especially suitable for applications in which the tube 18 will not be inflated in the area of the tunnel 54, such as shown in FIG. 7. Using a combination of guide(s) 32 and tunnel(s) 54 on a single platform 12 is also possible (e.g., tunnel 54 as illustrated with one or more guides 32 positioned on board 26 posteriorly of tunnel 54).

Figure 8:
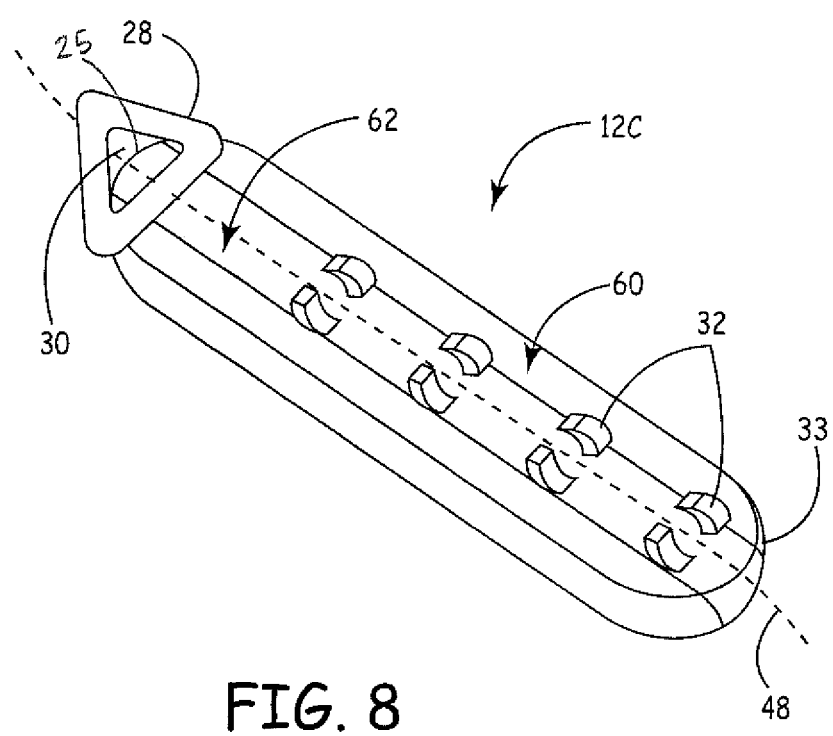
FIG. 8 is a top perspective view of a third embodiment of an exemplary platform.

FIG. 8 shows yet another embodiment of a platform 12C, which in an exemplary embodiment is substantially flat. Platform 12C includes a backboard 60 having a central guide track 62 disposed thereon. In one embodiment, backboard 60 is composed of a solid, soft, rubber-like material to comfortably fit on the floor of the nose. In another embodiment, backboard 60 is soft, hollow and inflatable to aid in placement and promote a tighter fit on the floor of the nose. Central guide track 62 is typically made of a more rigid plastic or metal that provides rigidity for insertion ease. In the illustrated embodiment, central guide track 62 has guides 32 thereon to provide guidance for tracking of inflatable tube 18.

Figure 10:
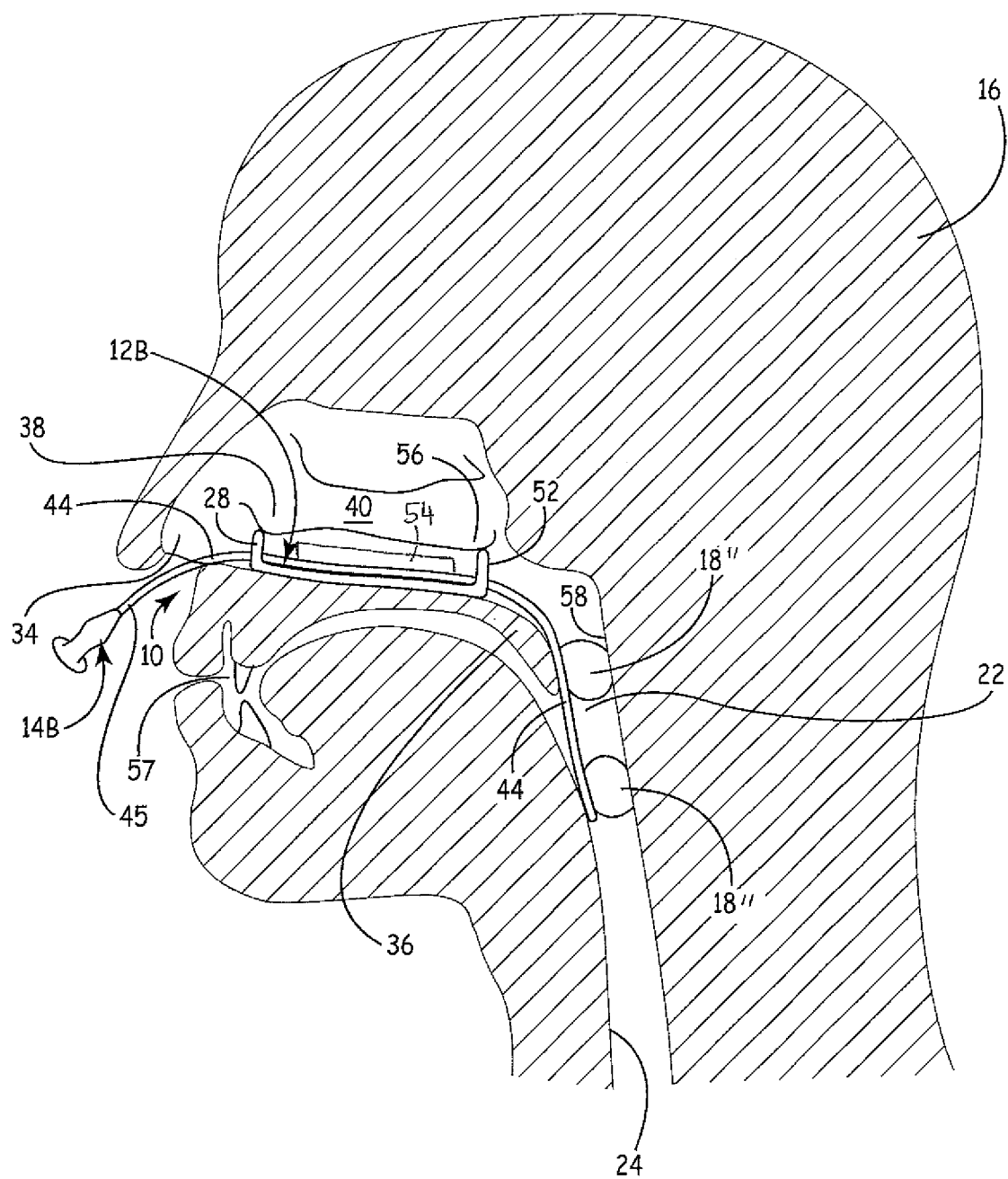
FIG. 10 is a sectional side view of a user having placed within his nasopharyngeal region a second embodiment of a platform and balloon catheter system of the present disclosure.

Referring to FIG. 10, in an exemplary method of use, a user 16 first inserts posterior support 52 of platform 12B into his/her nostril 34 and pushes platform 12B along the floor of his/her palate 36 until posterior support 52 is firmly lodged against the posterior aspect 56 of inferior turbinate 40 and anterior support 28 is firmly lodged against the anterior aspect 38 of inferior turbinate 40. To facilitate ease of use and comfort, either or both of anterior and posterior supports 28, 52 can be deflatable or otherwise collapsible for insertion and removal of platform 12B. In an exemplary embodiment, posterior support 52 is positionally fixed on platform 12B and the position of anterior support 28 on platform 12B is adjustable (or vice versa). This assures the most precise fit of platform 12B to a particular user 16 so that once positioned as desired, platform 12B does not move while in use.

The user 16 then guides a first end 42 of a lumen 44 of uninflated balloon catheter 14 through aperture 30 of anterior support 28, through tunnel 54 of board 26, and through aperture 30 of posterior support 52 until inflatable tube(s) 18 is in the desired position. As shown in FIG. 10, balloon catheter 14B includes two inflatable tubes 18".

Once in position, tubes 18" are inflated via the introduction of inflation fluid through lumen 44. The placement of tubes 18" as shown in FIG. 10 is especially suitable for snore respite. When inflated, the upper tube 18" prevents vibration of the posterior part of the palate 36 by keeping it spaced from the posterior pharyngeal wall 58, but not so much that breathing through the mouth 57 is inhibited. The lower tube 18" supports the base of the tongue 24 to enhance breathing. For some users, using only a single tube 18" (such as the upper tube 18" shown in FIG. 10) is all that may be needed for effective snore respite. Comparing FIG. 10 to FIG. 1, tube 18" of FIG. 10 is typically longer and wider than tube 18' of FIG. 1 because the area to be opened and/or filled is larger. An especially suitable tube 18" has a nearly elliptical cross sectional shape and is fairly flat and broad, with a height of about 1.0 to about 1.5 cm, a width of about 2.0 to about 2.5 cm, a length of about 1.5 cm to about 2.0 cm, and an average diameter of channel 50 of about 1.0 to about 1.7 cm. The disclosed system 10 offers a snoring reduction solution that is a removable posterior palatal support not requiring an invasive procedure such as surgical implantation.

The placement of tubes 18" as shown in FIG. 10 is also especially suitable for airway control for obtunded anesthesia patients. System 10 serves as a removable nasal trumpet. When inflated, the upper tube 18" opens the nasal airway by keeping the posterior part of the palate 36 spaced from the posterior pharyngeal wall 58, while the lower tube 18" supports the base of the tongue 24 and prevents it from falling back onto the posterior pharyngeal wall 58 as the user lies on his/her back during a procedure.

Because platform 12 extends only into an upper portion of a user's nasopharyngeal region, the platform 12 may be more easily tolerated than other supports that extend lower into the pharynx. In one embodiment, platform 12 has a downward curve adjacent its posterior end (as illustrated, for example, by curve C in FIGS. 1 and 2) while in another embodiment, platform 12 is generally planar (as illustrated, for example, in FIGS. 8 and 10). Moreover, because platform 12 is separate from balloon catheter 14, a single platform 12 can be sized for a particular patient and used with different catheters 14 having one or more balloons 18 of different diameters, lengths and shapes for various medical applications. Because each of anterior support 28 and posterior support 52 have apertures 30, and tubes 18 have channels 50, airflow through the user's nose is substantially maintained during use of system 10. Moreover, system 10 is used in only one nostril 34; therefore, the free nostril remains unobstructed.

In an exemplary method for removing system 10, a user (i.e., the person 16 in whose nose system 10 is deployed or the person's nurse or doctor) deflates the tubes 18 and pulls luer lock tubing 45 and lumen 44 out of the nostril 34 to remove balloon catheter 14. If applicable, the user can deflate or otherwise collapse anterior support 28 and posterior support 52. The user can then reach into nostril 34 to dislodge anterior support 28 and thereby pull out platform 12. Tweezers or other tools may be useful for this purpose.

The disclosed uses are merely illustrative. Many variations are possible in the number, placement, sizes and shapes of tubes 18 in any particular application of the disclosed system 10, as many different configurations are possible to treat a variety of medical conditions. Moreover, in another exemplary use, platform 12 may be used to guide a device other than a balloon catheter into a user's nasopharyngeal region. Another suitable device, for example, includes a nasal irrigation device. The irrigation tubing would be passed through the platform 12 and positioned to irrigate from the floor of the nose superiorly and posteriorly. An embodiment of such an irrigation device having about two to three exit ports within the nasal vault and about six to nine ports positioned in the nasopharyngeal region rinse the nasopharynx more completely than existing irrigation systems. Moreover, monitoring devices can also be used with the disclosed system, such as, for example, an oxygen saturation monitoring device to determine the amount of pressure needed in the tubes 18.

Although the subject of this disclosure has been described with reference to several embodiments, workers skilled in the art will recognize that changes may be made in form and detail without departing from the spirit and scope of the disclosure. In addition, any feature disclosed with respect to one embodiment may be incorporated in another embodiment, and vice-versa.

What is claimed is:

1. A system including:
   a platform configured tor insertion into a user's nostril, the platform including:
      a board having first and second major surfaces; and
      a support extending from the board, the support comprising an aperture therethrough; and
   a catheter including:
      an inflatable tube; and
      a lumen having first and second ends, the first end connected to the tube and the second end connected to a pressurized fluid source for inflating the tube;
   wherein the tube is configured for insertion through the aperture;
   wherein the platform includes a guide disposed on the board; and
   wherein the guide is one of a plurality of guides being arranged in pairs, a path between each pair of guides configured to allow passage of the tube.

2. The system of claim 1 wherein at least one or the first and second major surfaces of the board is curved.

3. The system of claim 1 wherein the guide includes a channel therethrough.

4. The system of a claim 1 wherein the support is substantially triangular.

5. The system of claim 1 wherein the support is inflatable.

6. The system of claim 1 wherein at least a portion of the board is inflatable.

7. The system of claim 1 wherein the tube has a substantially triangular shape.

8. The system of claim 1 wherein the tube has a substantially rhombus shape.

* * * * *